United States Patent [19]

Barrett

[11] Patent Number: 4,997,442
[45] Date of Patent: Mar. 5, 1991

[54] BICOMPOSITE INTRAOCULAR LENSES

[75] Inventor: Graham D. Barrett, Perth, Australia

[73] Assignee: Alcon Laboratories, Inc., Fort Worth, Tex.

[21] Appl. No.: 347,362

[22] Filed: May 4, 1989

[51] Int. Cl.$^5$ .............................................. A61F 2/16
[52] U.S. Cl. .................................... 623/6; 623/901
[58] Field of Search .................................... 623/6, 901

[56] References Cited

U.S. PATENT DOCUMENTS

| | | | |
|---|---|---|---|
| 4,242,762 | 1/1981 | Tennant | 623/6 |
| 4,254,509 | 3/1981 | Tennant | 623/6 |
| 4,254,510 | 3/1981 | Tennant | 623/6 |
| 4,468,820 | 9/1984 | Uhler | 623/6 |
| 4,476,591 | 10/1984 | Arnott | 623/6 |
| 4,601,722 | 7/1986 | Kelman | 623/6 |
| 4,615,702 | 10/1986 | Koziol | 623/6 |
| 4,624,670 | 11/1986 | Bechert | 623/6 |
| 4,629,461 | 12/1986 | Clayman | 623/6 |
| 4,634,441 | 1/1987 | Clayman | 623/6 |
| 4,664,666 | 5/1987 | Barrett | 623/6 |
| 4,666,444 | 5/1987 | Pannu | 623/6 |
| 4,787,904 | 11/1988 | Severin | 623/6 |

OTHER PUBLICATIONS

Apple, et al., *Evolution of Intraocular Lenses*, Department of Ophthalmology and Pathology, University of Utah Health Sciences Center, Salt Lake City, Utah (Printed by University of Utah, 1985), pp. 1-23 & 4 cover pp. 623-626.

*Primary Examiner*—Ronald Frinks
*Attorney, Agent, or Firm*—James A. Arno; Sally S. Yeager

[57] ABSTRACT

Bicomposite, hydrogel intraocular lenses with one or more haptic portions having a lower water content than the corresponding optic portions, and methods for their manufacture are disclosed. The bicomposite lenses are manufactured by (i) preparing a bicomposite button of hydrogel material containing one or more polymers or copolymers; (ii) lathing the button to produce a dehydrated intraocular lens with an optic and at least one haptic; and (iii) hydrating the lens.

14 Claims, No Drawings

BICOMPOSITE INTRAOCULAR LENSES

BACKGROUND OF THE INVENTION

The present invention relates to bicomposite intraocular lenses. More particularly, the intraocular lenses comprise a high water hydrogel optic portion and a relatively low water hydrogel haptic portion. In addition, the present invention is directed towards methods for manufacturing the bicomposite intraocular lenses.

The most commonly used material for intraocular lenses (IOLs) has been polymethylmethacrylate (PMMA). However, PMMA lenses have been shown to be injurious to the corneal endothelium. The maintenance of corneal clarity is dependent on the endothelium which is essentially nonregenerative. It appears there is a biophysical interaction between the hydrophobic PMMA and the endothelium, such that even the slightest touch on insertion of the IOL will cause significant endothelial cell disruption by adherence of the cells to the lens surface.

U.S. Pat. No. 4,664,666 issued to Barrett, May 12, 1987, discloses a hydrophilic intraocular lens. These lenses are formed of hydrogels which when hydrated are soft and flexible and have been found to cause little endothelial damage on contact. These intraocular lenses, due to the mechanical properties of available hydrogel materials, are limited to configurations having flange type haptics rather than loop type haptics. However, the flange type haptics disclosed therein are not of a conventional loop type configuration; and as a result there can be difficulty in positioning and seating the lenses in the eye. The haptics can not be formed as conventional loop haptics due to the nature of the hydrogel material which is used for the entire IOL, including the optic portion and the haptic portion. If formed as loop haptics, the high water content haptics are not strong enough, or rigid enough, to support the optic portion of the IOL within the eye.

U.S. Pat. No. 4,242,762 issued to Tennant, Jan. 6, 1981 discloses intraocular lenses wherein the haptic and the optic are preferably manufactured as a single unit and formed of the same material. However, the optic may be formed of a different material and fused to the haptic. For example, Tennant discloses an optic formed of p-HEMA with the haptic being formed of PMMA. However, this IOL with its rigid haptic portion cannot be folded or deformed like the IOLs disclosed in U.S. Pat. No. 4,664,666. In addition the use of PMMA haptics, like PMMA lenses, can be harmful to the corneal endothelium. U.S. Pat. No. 4,254,509 issued to Tennant, Mar. 10, 1981 discloses intraocular lenses wherein the optic is made of a rigid material such as PMMA and the haptic portion is made of a soft material such as p-HEMA. U.S. Pat. No. 4,254,510 issued to Tennant, Mar. 10, 1981, discloses an intraocular lens wherein the optic portion of the intraocular lens may be of rigid material such as PMMA and the limbs or haptics can be made of PMMA or a softer material such as p-HEMA.

It is an object of the present invention to provide for intraocular lenses which have the advantages of a hydrogel type lens, but with conventional loop type haptics that allow for proper positioning and seating of the IOL in the eye.

It is another object of this invention to provide methods for producing the lenses.

SUMMARY OF THE INVENTION

The present invention is directed to bicomposite intraocular lenses. The optic portion of the IOL comprises a deformable relatively high water content hydrogel. The haptic portion of the IOL comprises a relatively low water content hydrogel with relatively high strength and rigidity which is polymerized with or otherwise adhered to the optic portion.

The present invention also includes methods for manufacturing the bicomposite intraocular lenses. For example, in one method, the polymer forming the haptics is polymerized in a mold in which is then bored a hole in which the polymer which forms the optic portion of the IOL is then polymerized. The haptic portion can then be milled to form haptics and the optic portion can be lathed as desired.

In another method, the polymer forming the haptics is polymerized around a rod having the diameter desired of the optic portion of the IOL. The rod is then removed and the polymer to be used as the optic portion of the lens is polymerized within the space left after the rod is removed. Again the IOL can then be lathed and milled as in method one.

Another method for manufacturing the bicomposite lenses comprises conventional rod casting.

Additionally, IOLs comprising an optic which has a relatively higher water content than the haptic portion can be made by making a rod or column, of a polymer or copolymer and then tempering, physically or chemically, an outer ring of the rod to form a dehydrated portion which can be lathed or otherwise worked to form haptics, said haptics on hydration having a lower water content than the optic of the resulting IOL. Conversely, an inner area of the rod can be tempered such that after lathing the rod to form a dehydrated IOL and then hydrating the IOL, the optic has a higher water content than the haptics lathed and hydrated from the untempered portion of the rod.

DETAILED DESCRIPTION OF PREFERRED EMBODIMENTS

The intraocular lenses of the present invention comprise a high water, low strength optic portion and a relatively lower water, high strength haptic portion. It is the optic portion of the intraocular lens which functions like the natural lens of the eye. The haptic portion of the intraocular lens functions to hold the optic portion in place within the eye. Both the optic portion and the haptic portion are made of hydrogel type polymers, therefore the IOLs of the present invention have the advantages of prior hydrogel IOLs. However, because the haptic portion has a lower water content than prior hydrogel IOLs, or the optic portion of the present IOLs, they can be ground, in their dehydrated form, into conventional loop type haptics. On hydration the hydrogel loop type haptics are strong and rigid enough to support the relatively weak, flexible optic portion in the eye. However, because the haptics comprise a hydrogel material, they are hydrophilic and less likely, on contact, to cause damage to the eye, particularly the endothelium, iris pigment epithelium and ciliary epithelium.

Typically, intraocular lenses can be placed in the anterior or posterior chamber of the eye. The various configurations of the lenses disclosed herein provide for placing the lens in either the anterior or posterior chamber.

For purposes of the present specification "hydrogels" are crosslinked polymers which on hydration have an equilibrium content of between about 5% and 95% percent water. The optic portion of the bicomposite IOLs can be formed using any suitable hydrogel which will provide for the desired elements of the optic of the IOL of the present invention, such as transparency, flexibility and hydrophilicity. The optic will preferably have a water content of at least about 25%.

The preferred optic hydrogel comprises a copolymer of hydroxyethylmethacrylate (HEMA) and ethoxyethyl methacrylate at a ratio of about 75% HEMA TO 25% ethoxyethyl methacrylate. Other hydrogels can comprise, for example, copolymers of vinyl pyrrolidone and HEMA or methyl methacrylate; copolymers of glyceral methacrylate and methyl methacrylate; copolymers of HEMA/diacetone acyl amide and various polymers and copolymers comprising the following monomers: hydroxyalkyl methacrylates and acrylates with the alkyl groups having from 2 to 6 carbon atoms; vinyl hydroxy acetate, vinyl hydroxy propionate, vinyl hydroxy butyrate; N-vinyl lactams namely N-vinyl pyrrolidone, N-vinyl caprolactam and N-vinyl piperidone; N,N dialkyl amino ethyl methacrylates and acrylates with the alkyl groups having from 0 to 2 carbon atoms; hydroxyalkyl vinyl ethers with the alkyl groups having 2 to 4 carbon atoms; 1-vinyloxy 2-hydroxyethylene, 1-vinyloxy 5-hydroxy 3-oxapentane, 1-vinyloxy 8-hydroxy 3,6-dioxaoctane, 1-vinyloxy 14-hydroxy 3,6,9,12 tetraoxatetradectane; N-vinyl morpholine; N,N dialkyl acrylamide with the alkyl groups having from 0 to 2 carbons atoms; alkyl vinyl ketone with the alkyl group having 1 to 2 carbon atoms; N-vinyl succinimide and N-vinyl glutarimide; N-vinyl imidazole; and N-vinyl 3-morpholinone.

The haptic portion of the intraocular lens is also a hydrogel but has a relatively low water content compared to the optic portion of the IOL. The water content of the haptics can be as low as about 5%. This low water hydrogel can be any polymer or copolymer which will allow for a self supporting IOL, i.e., the haptics are rigid enough to allow for construction of narrow diameter loop type haptic(s) with force/displacement characteristics similar to or better than conventional loop haptics such as those disclosed in U.S. Pat. Nos. 4,601,722; 4,615,702; 4,624,670; 4,629,461; 4,634,441; 4,666,444; 4,468,820; and 4,476,591. Also, see, Apple et al. *Evolution of Intraocular lenses*. Department of Ophthalmology and Pathology, University of Utah Health Sciences Center, Salt Lake City, Utah, (Printed by University of Utah, 1985) (p.6, Dannheim lens; p.7, Barraquer, J-loop lens; p.9, Brinkhorst lens; p.13, Leiske, Optiflex, Kelman Quadraflex, Kelman Omnifit and Kelman multiflex lenses; p.14, lenses; p.15 lenses; the Shearing J-loop on p.17; and the lenses depicted on pp.18–22).

The preferred hydrogel for the haptic portion is a copolymer of HEMA and methylmethacrylate (MMA). The percentage of HEMA is preferably less than about 50%, most preferably between about 25–50% HEMA. Other polymers and copolymers which can be used to form the haptic portion of the bicomposite IOL will typically include: copolymers of vinyl pyrrolidone and HEMA or methyl methacrylate; copolymers of glyceral methacrylate and methyl methacrylate; copolymers of HEMA/diacetone acyl amide and various polymers and copolymers comprising combinations of the following monomers: hydroxyalkyl methacrylates and acrylates with the alkyl groups having from 2 to 6 carbon atoms; vinyl hydroxy acetate, vinyl hydroxy propionate, vinyl hydroxy butyrate; N-vinyl lactams namely N-vinyl pyrrolidone, N-vinyl caprolactam and N-vinyl piperidone; N,N Dialkyl amino ethyl methacrylates and acrylates with the alkyl groups having from 0 to 2 carbon atoms; hydroxyalkyl vinyl ethers with the alkyl groups having 2 to 4 carbon atoms; 1-vinyloxy 2-hydroxyethylene, 1-vinyloxy 5-hydroxy 3-oxapentane, 1-vinyloxy 8-hydroxy 3,6-dioxaoctane, 1-vinyloxy 14-hydroxy 3,6,9,12 tetraoxatetradectane; N-vinyl morpholine; N,N dialkyl acrylamide with the alkyl groups having from 0 to 2 carbons atoms; alkyl vinyl ketone with the alkyl group having 1 to 2 carbon atoms; N-vinyl succinimide and N-vinyl glutarimide. N-vinyl imidazole; and N-vinyl 3-morpholinone.

In addition the optic and/or the haptic portion can also include an ultraviolet (U.V.) absorbing compound such as benzotriazoles, which can be polymerized with the optic and/or the haptic portions of the bicomposite lens of the present invention. The U.V. absorbers disclosed in the pending Patent application No. 198,904, incorporated herein by reference, can be copolymerized with the polymers used to form the hydrogels for the optics and haptics of the invention. Of those UV absorbers, 2[2-hydroxy-4-methacryloxy(2'-hydroxy-3'-propoxy)]2H-4-chlorobenzotriazole is most preferred.

This invention is also directed to methods for production of the bicomposite intraocular lenses. For example, one method for their production includes: making a button by polymerizing the polymer or copolymer for forming the haptics in a mold; boring the polymer to the extent that the bore is equal to the desired diameter of the optic portion; and polymerizing the desired optic polymer or copolymer within the core. The resulting dehydrated cylinder is lathed to form "buttons" which are approximately 8mm in diameter and 1mm thick. The button is then lathed according to conventional methods known to those skilled in the art to produce an IOL with an optic and haptic(s), which on hydration, are characterized by a soft, flexible optic and rigid, but hydrophilic haptic(s).

Another method for lens production comprises polymerizing the haptic polymer or copolymer around a rod with a diameter equal to the optic portion; removing the rod and polymerizing the optic polymer or copolymer within the core. The resulting rod is milled to produce buttons which are lathed and hydrated according to conventional methods to produce bicomposite IOLs encompassed by the present invention.

Further methods for producing the intraocular lenses of the present invention can comprise rod casting and tempering techniques. The word "tempering", as used herein means, any chemical or physical means to treat a polymer or copolymer so that on hydration the treated portion has either a lower or higher water content, depending on the type of tempering used, than the untreated polymer or copolymer. Tempering techniques comprise the making of buttons or rods of a polymer or copolymer which is then physically or chemically tempered to either change an outer ring portion or an inner core of the rod or button. Tempering of the outer ring portion of the rod can be done to form an outer ring of polymer or copolymer which on hydration will have a lower water content than the core. Prior to hydration the outer ring is worked to form haptics and the core lathed to form an optic with the characteristics of the present invention as described above. Alternatively, the inner core portion of a solid rod can be tempered such that after conventional lathing and hydration is complete, the resulting IOLs will comprise bicomposite lenses as described herein.

The following examples are included to illustrate the invention but should not be considered as limiting.

EXAMPLE 1

A bicomposite IOL comprising a HEMA optic and a haptic made of a copolymer of HEMA and methylmethacrylate (MMA) was made according to the following procedure.

HEMA monomer was purified by neutralization followed by distillation to remove impurities and inhibitor and MMA (50%) was then added to the HEMA. Ethylene glycol dimethacrylate (EGDMA) (0.5%) was added to the HEMA/MMA as a cross-linking agent. Azobisisobutyronitrile (AIBN) (0.5%) was added as an initiator. This mixture was agitated by ultrasound to ensure complete dissolution of the initiator. The mixture was then poured into 15mm × 15mm injection molded polypropylene cylindrical molds which were sealed and flushed with either argon or nitrogen.

The molds were then placed in a temperature controlled water bath for 36 hours. The temperature during that period was gradually increased with a temperature controller to a maximum temperature of 80° C. The molds were then post cured in an oven at 100° C. for 3 hours.

The resulting HEMA/MMA copolymer (50% HEMA/50% MMA) was removed from the molds and a 6mm hole was drilled into each cylinder to a depth of 13mm. The bored cylinders were placed back into the 15mm × 15mm molds and a solution of purified HEMA monomer, ethylene glycol dimethacrylate (0.5%) and (AIBN) (0.5%) was poured into the holes. The molds were then sealed and placed in a water bath for 36 hours during which time the temperature was raised by a temperature controller to 80° C.

The resulting cylinders were removed from the molds and the tops, bottoms and edges lathed to form "buttons" 1mm thick with a diameter of about 8mm. The resulting buttons in dehydrated form consisted of a central core (6mm diameter) of HEMA surrounded by a ring of HEMA/MMA. The buttons were conventionally lathed to form IOLs with a lens with a HEMA optic of 6mm and a surrounding concentric haptic of 8mm. The IOLs were than hydrated producing a lens with a soft, flexible optic of about 7.08mm with a rigid, yet hydrophilic haptic of about 8mm.

EXAMPLE 2

A button was made as described in Example 1. The button was conventionally lathed by a computer controlled lathe to produce an IOL with a 6mm optic and conventional style loop haptics. On hydration, the IOL had a soft flexible optic and relatively rigid loop haptics.

EXAMPLE 3

Buttons with compositions as described below, were made as described in Example 1. The buttons were then lathed and hydrated, as described in Example 1, to produce IOLs.

| IOL | Optic | Haptic (HEMA/MMA) |
| --- | --- | --- |
| 1 | HEMA | 70/30 |
| 2 | HEMA | 60/40 |
| 3 | HEMA | 50/50 |
| 4 | HEMA | 40/60 |
| 5 | HEMA | 30/70 |

EXAMPLE 4

The procedures of Example 1 were followed to produce IOLs wherein the optic was made of HEMA/ethoxyethylmethacrylate (80%/20%) and the haptics were made of HEMA/MMA (50%/50%). The optic portion had improved mechanical strength compared to HEMA and an improved refractive index (approximately 1.45) compared to HEMA (refractive index 1.435). However, the optic was as flexible as a 100% HEMA optic and demonstrated rapid recovery following deformation.

I claim:

1. A self supporting bicomposite intraocular lens suitable for implantation in the human eye to replace the natural crystalline lens, comprising:
   an optic portion comprising a hydrogel capable of being folded; and
   a haptic portion comprising a hydrogel, which in its hydrated state has lower water content than the hydrated optic portion.

2. The intraocular lens of claim 1 wherein the optic portion has a water content between about 5% and 95%.

3. The intraocular lens of claim 2 wherein the water content is at least about 25%.

4. The intraocular lens of claim 1 wherein the haptic has a water content of at least about 5%.

5. The intraocular lens of claim 1 wherein the optic portion comprises copolymers selected from the group consisting of:
   HEMA/ethoxyethylmethacrylate, HEMA/vinylpyrrolidone, HEMA/MMA, glyceralmethacrylate/MMA, HEMA/diacetone acylamide; and polymers or copolymers comprising monomers selected from the group consisting of: hydroxyalkyl methacrylates and acrylates with the alkyl groups having from 2 to 6 carbon atoms; vinyl hydroxy acetate, vinyl hydroxy propionate, vinyl hydroxy butyrate; N-vinyl lactams namely N-vinyl pyrrolidone, N-vinyl caprolactam and N-vinyl piperidone; N,N dialkyl amino ethyl methacrylates and acrylates with the alkyl groups having from 0 to 2 carbon atoms; hydroxyalkyl vinyl ethers with the alkyl groups having 2 to 4 carbon atoms; 1-vinyloxy 2-hydroxyethylene, 1-vinyloxy 5-hydroxy 3-oxapentane, 1-vinyloxy 8-hydroxy 3,6dioxaoctane, 1-vinyloxy 14-hydroxy 3,6,9,12 tetraoxatetradecane; N-vinyl morpholine; N,N dialkyl acrylamide with the alkyl groups having from 0 to 2 carbons atoms; alkyl vinyl ketone with the alkyl group having 1 to 2 carbon atoms; N-vinyl succinimide and N-vinyl glutarimide; N-vinyl imidazole; and N-vinyl 3morpholinone.

6. The intraocular lens of claim 1 wherein the haptic portion comprises a copolymer selected from the group consisting of: HEMA/ethoxyethylmethacrylate, HEMA/vinylpyrrolidone, HEMA/MMA, glyceralmethacrylate/MMA, HEMA/diacetone acylamide; and polymers or copolymers comprising monomers selected from the group consisting of: hydroxyalkyl methacrylates and acrylates with the alkyl groups having from 2 to 6 carbon atoms; vinyl hydroxy acetate, vinyl hydroxy propionate, vinyl hydroxy butyrate; N-vinyl lactams namely N-vinyl pyrrolidone, N-vinyl caprolactam and N-vinyl piperidone; N,N dialkyl amino ethyl methacrylates and acrylates with the alkyl groups having from 0 to 2 carbon atoms; hydroxyalkyl vinyl ethers with the alkyl groups having 2 to 4 carbon atoms; 1-vinyloxy 2-hydroxyethylene, 1-vinyloxy 5-hydroxy 3-oxapentane, 1-vinyloxy 8-hydroxy 3,6-dioxaoctane, 1-vinyloxy 14-hydroxy 3,6,9,12 tetraoxatetradectane; N-vinyl morpholine; N,N dialkyl acrylamide with the alkyl groups having from 0 to 2 carbons atoms; alkyl vinyl ketone with the alkyl group having 1 to 2 carbon atoms; N-vinyl succinimide and N-vinyl glutarimide; N-vinyl imidazole; and N-vinyl 3-morpholinone.

7. The intraocular lens of claim 1 wherein the optic comprises a copolymer of HEMA and ethoxyethylmethacrylate.

8. The intraocular lens of claim 7 wherein the HEMA concentration is 75% and the ethoxyethylmethacrylate concentration is 25%.

9. The intraocular lens of claim I wherein the haptic comprises a copolymer of HEMA and MMA.

10. The intraocular lens of claim 9 wherein the percentage of HEMA is less than about 50%.

11. The intraocular lens of claim 9 wherein the percentage of HEMA is between about 25 and 50%.

12. A bicomposite intraocular lens comprising:
an optic comprising a copolymer of HEMA and ethoxyethylmethacrylate; and
a haptic portion comprising a copolymer of HEMA and MMA.

13. The intraocular lens of claim 12 wherein in the optic the percentage of HEMA is 75% and ethoxyethylmethacrylate is 25%; and in the haptic the percentage of HEMA is between about 25 and 50%.

14. A method for manufacturing a bicomposite, hydrogel intraocular lens having a higher water content in the optic portion than in the haptic portion, which comprises:
(a) manufacturing a bicomposite button comprising one or more polymers or co-polymers;
(b) lathing the button to produce a dehydrated intraocular lens with an optic and at least one haptic; and
(c) hydrating the dehydrated intraocular lens.

* * * * *